(12) United States Patent
Zhang

(10) Patent No.: US 9,730,596 B2
(45) Date of Patent: Aug. 15, 2017

(54) LOW POWER BIOLOGICAL SENSING SYSTEM

(71) Applicant: STMicroelectronics, Inc., Coppell, TX (US)

(72) Inventor: John H. Zhang, Fishkill, NY (US)

(73) Assignee: STMicroelectronics, Inc., Coppell, TX (US)

(*) Notice: Subject to any disclaimer, the term of this patent is extended or adjusted under 35 U.S.C. 154(b) by 953 days.

(21) Appl. No.: 13/931,138

(22) Filed: Jun. 28, 2013

(65) Prior Publication Data
US 2015/0005610 A1  Jan. 1, 2015

(51) Int. Cl.
*A61B 5/04* (2006.01)
*A61B 5/00* (2006.01)
(Continued)

(52) U.S. Cl.
CPC .......... *A61B 5/04001* (2013.01); *A61B 5/688* (2013.01); *A61B 5/6877* (2013.01);
(Continued)

(58) Field of Classification Search
CPC .. A61N 1/0551; A61N 1/0529; A61N 1/3605; A61N 1/0556; A61N 1/0558; A61N 1/08; A61N 1/36017; A61N 1/0531; A61N 1/0539; A61N 1/0565; A61N 1/36025; A61N 1/3606; A61B 5/04001; A61B 5/0478; A61B 2562/0285; H01L 29/413; H01L 29/41766; H01L 29/42392; H01L 29/456; H01L 29/4908; H01L 29/66431;
(Continued)

(56) References Cited

U.S. PATENT DOCUMENTS 7,844,347 B2 * 11/2010 Brabec ................. A61N 1/0556
600/372
7,902,639 B2   3/2011 Garrou et al.
(Continued)

OTHER PUBLICATIONS

"Rolling up a Graphene Sheet". Calvaresi et al. ChemPhysChem. vol. 14, pp. 3447-3453. Dec. 2, 2013.*
(Continued)

*Primary Examiner* — Joseph Stoklosa
*Assistant Examiner* — Brian M Antiskay
(74) *Attorney, Agent, or Firm* — Seed IP Law Group LLP

(57) ABSTRACT

It is recognized that, because of its unique properties, graphene can serve as an interface with biological cells that communicate by an electrical impulse, or action potential. Responding to a sensed signal can be accomplished by coupling a graphene sensor to a low power digital electronic switch that is activatable by the sensed low power electrical signals. It is further recognized that low power devices such as tunneling diodes and TFETs are suitable for use in such biological applications in conjunction with graphene sensors. While tunneling diodes can be used in diagnostic applications, TFETs, which are three-terminal devices, further permit controlling the voltage on one cell according to signals received by other cells. Thus, by the use of a biological sensor system that includes graphene nanowire sensors coupled to a TFET, charge can be redistributed among different biological cells, potentially with therapeutic effects.

20 Claims, 12 Drawing Sheets

(51) Int. Cl.
    *A61N 1/00* (2006.01)
    *G01N 27/414* (2006.01)
    *B82Y 30/00* (2011.01)
(52) U.S. Cl.
    CPC .......... *B82Y 30/00* (2013.01); *G01N 27/4145* (2013.01); *Y10T 29/4913* (2015.01)
(58) Field of Classification Search
    CPC ............. H01L 29/66636; H01L 29/775; H01L 51/0558
    USPC ................ 600/372–373, 377–378, 393, 395, 600/544–545; 607/115–118
    See application file for complete search history.

(56) References Cited

U.S. PATENT DOCUMENTS

| 7,960,721 | B2 | 6/2011 | Belcher et al. | |
| 8,489,203 | B2* | 7/2013 | Ortmann | A61B 5/04001 |
| | | | | 600/377 |
| 8,774,890 | B2* | 7/2014 | Ready | A61N 1/05 |
| | | | | 600/377 |
| 2004/0133118 | A1* | 7/2004 | Llinas | A61B 5/04001 |
| | | | | 600/544 |
| 2008/0213663 | A1 | 9/2008 | Hu et al. | |
| 2008/0319506 | A1* | 12/2008 | Cauller | A61N 1/0536 |
| | | | | 607/46 |
| 2009/0248113 | A1* | 10/2009 | Nimer | A61N 1/05 |
| | | | | 607/60 |
| 2010/0305657 | A1* | 12/2010 | Park | B82Y 5/00 |
| | | | | 607/45 |
| 2014/0222123 | A1* | 8/2014 | Cui | A61N 1/0472 |
| | | | | 607/115 |

OTHER PUBLICATIONS

Ionescu et al., "Tunnel field-effect transistors as energy-efficient electronic switches," *Nature* 479:329-337, 2011.
Meric et al., "High-frequency performance of graphene field effect transistors with saturating IV-characteristics," IEDM11-15, IEEE, 2011, 2.1.1-2.1.4.
Riel et al., "InAs—Si Heterojunction Nanowire Tunnel Diodes and Tunnel FETs," IEDM12-391, IEEE, 2012, 16.6.1-16.6.4.
Scarselli et al., "Electronic and optoelectronic nano-devices based on carbon nanotubes," *J. Phys. Condens. Matter* 24:313202, 2012. (37 pages).

* cited by examiner

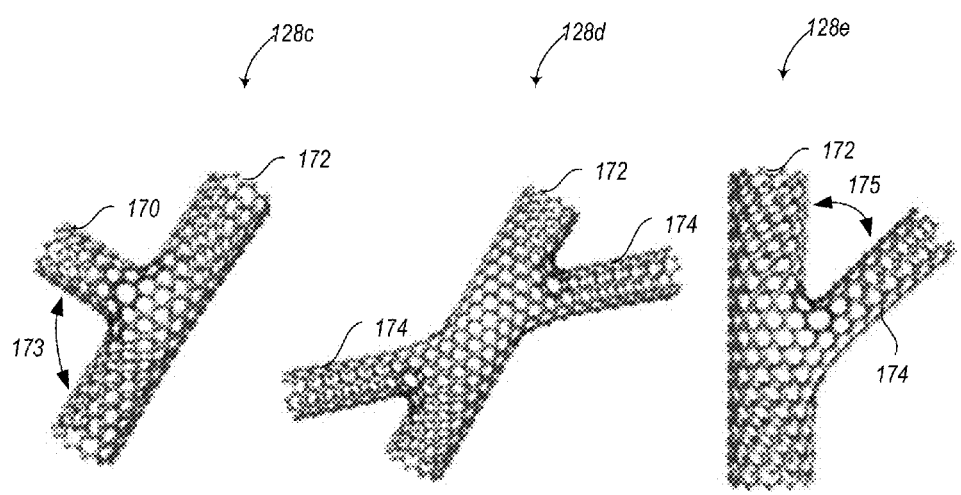
*Fig. 12A*  *Fig. 12B*  *Fig. 12C*
(Prior Art)  (Prior Art)  (Prior Art)

LOW POWER BIOLOGICAL SENSING SYSTEM

BACKGROUND

Technical Field

The present disclosure relates to the fabrication of low power tunneling diodes and tunneling field effect transistors (TFETs) used in conjunction with graphene sensors for biological applications.

Description of the Related Art

Tunneling diodes and TFETs are microelectronic devices that switch on and off in response to a relatively low applied voltage, making them good candidates for low power applications. While a state-of-the-art 3-D multi-gate transistor requires applying about 0.8 V to switch on, a tunneling device requires applying less than about 0.5 V. Consistent with the reduction in applied voltage, the TFET device achieves the same performance as a bulk silicon MOSFET device using about half the energy, when operated in a low-energy regime. As a result, less power is consumed by the tunneling device and less power is dissipated as heat. Thus, the TFET is advantageous for use within a certain energy range, e.g., for relatively low energy applications. [A. M. Ionescu and H. Riel, "*Tunnel Field-Effect Transistors as Energy-Efficient Electronic Switches*," Nature: 479, pp. 329-337, Nov. 17, 2011, herein incorporated by reference in its entirety].

Graphene has drawn attention in recent years for use in FETs due to its extraordinary material properties, as shown in FIGS. 1A and 1B. Graphene is a monolayer of carbon graphite atoms arranged in a honeycomb crystal lattice (FIG. 1A). Crystalline graphite is made of stacked sheets of graphene. Although graphene was known for many years, a single graphene sheet was not isolated until 2004, for which a Nobel Prize in physics was awarded in 2010. Mechanically, graphene is one of the strongest materials ever tested, more than 100 times stronger than steel (if steel could be made as thin as a graphene sheet). Graphene sheets are flexible and can be rolled into carbon nanotubes or formed into nanowires or graphene nanoribbons. Graphene is also very lightweight, weighing only 0.77 mg per square meter (FIG. 1B).

Graphene also has favorable electronic properties. For example, graphene has high electron mobility over a wide temperature range, lower resistance at room temperature than any known material, and low noise. Furthermore, a graphene film can be epitaxially grown on silicon carbide (SiC) by heating the SiC in a vacuum chamber to temperatures exceeding 1100° C. The graphene film can then be patterned using conventional microelectronics techniques. Graphene has been studied as a material for use in microelectronics, such as in graphene field effect transistors (GFETs) [Meric, et al., *Proceedings of the IEEE IEDM Conference*, Dec. 5-7, 2011, pp. 2.1.1-2.1.4].

BRIEF SUMMARY

The properties of graphene are recognized as having application in the field of biological sensors. From a chemical standpoint, graphene's stability makes it impervious to harsh ionic solutions found in biological environments, including the human body. From a structural standpoint, graphene's flexibility allows it to be made into a nanowire that can be bent to attach to and/or wrap around delicate biological tissues. From an electrical standpoint, graphene's ability to conduct electrical signals suggests that the material can serve as an interface with biological cells that communicate by an electrical impulse, or action potential (e.g., neurons, muscle cells, endocrine cells, and certain types of plant cells).

The size of a typical nucleus of a human neuron, for example, is within the range of about 1-20 µm, or 1000-20,000 nm. Thus, neurons can be probed by a sub-micron or nanometer sized sensor. Voltage levels associated with nerve cell activity are relatively weak, and therefore a very sensitive sensor is needed. In addition, the conduction path for electrical signals transmitted from the cell to the sensor, and from the sensor to external destinations, is desirably characterized by low loss. Furthermore, heat generated by electrical devices implanted within a live organism is generally undesirable, and should be minimized. Graphene offers all of the above characteristics that make it a suitable material for sensing low power electrical signals originating from within a biological organism. However, graphene is not capable of switching in response to those signals. Graphene, being neither a conductor nor a semiconductor, fails to exhibit a band gap, an electrical property that is beneficial for use in digital logic circuits.

Responding to a sensed signal can be accomplished, however, by coupling a graphene sensor to a low power diode switch or a transistor switch that is activatable by the sensed low power electrical signals. It is recognized that low power devices such as tunneling diodes and TFETs are suitable for use in biological applications, (e.g., applications involving neurons) in conjunction with graphene sensors. While tunneling diodes can be used in diagnostic applications, TFETs, which are three-terminal devices, further permit controlling the voltage on one cell according to signals received by other cells. Thus, by the use of a biological sensor system that includes a graphene nanowire sensor coupled to a TFET, charge can be redistributed among different biological cells, potentially with therapeutic effects.

BRIEF DESCRIPTION OF THE SEVERAL VIEWS OF THE DRAWINGS

In the drawings, identical reference numbers identify similar elements. The sizes and relative positions of elements in the drawings are not necessarily drawn to scale.

FIGS. 12A-12C show three alternative form factors for a graphene nanotube sensor geometry that includes branches.

DETAILED DESCRIPTION

Figure 1A:
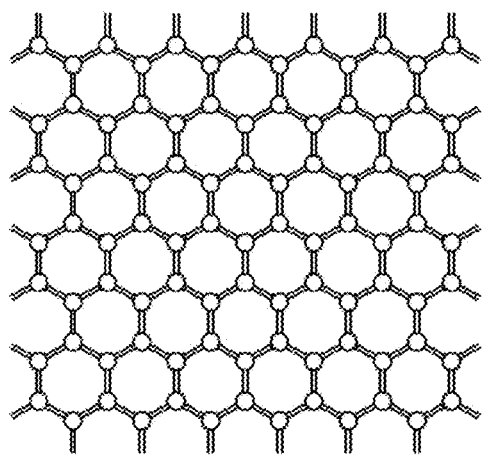
FIG. 1A is a molecular diagram showing the cellular structure of graphene.
Figure 1B:
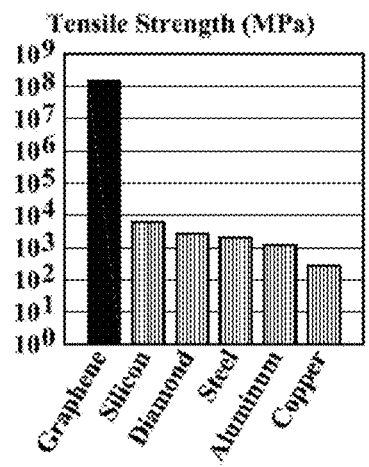
FIG. 1B is a series of bar graphs comparing properties of graphene against those of other materials.
Figure 1B:
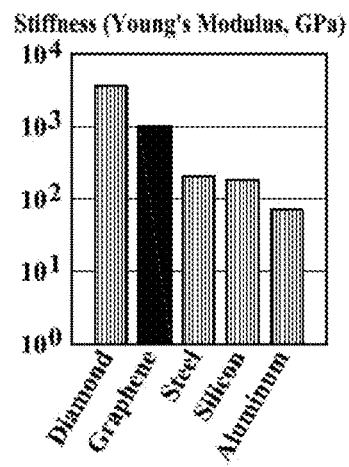
Figure 1B:
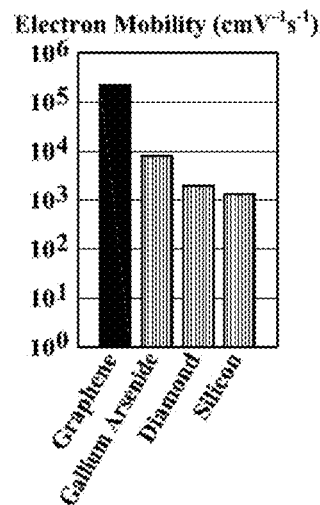
Figure 1B:
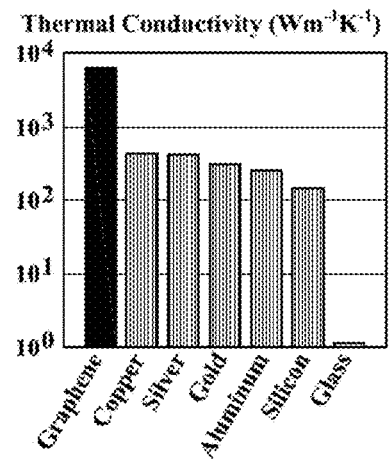

In the following description, certain specific details are set forth in order to provide a thorough understanding of various aspects of the disclosed subject matter. However, the disclosed subject matter may be practiced without these specific details. In some instances, well-known structures and methods of semiconductor processing comprising embodiments of the subject matter disclosed herein have not been described in detail to avoid obscuring the descriptions of other aspects of the present disclosure.

Unless the context requires otherwise, throughout the specification and claims that follow, the word "comprise" and variations thereof, such as "comprises" and "comprising" are to be construed in an open, inclusive sense, that is, as "including, but not limited to."

Reference throughout the specification to "one embodiment" or "an embodiment" means that a particular feature, structure, or characteristic described in connection with the embodiment is included in at least one embodiment. Thus, the appearance of the phrases "in one embodiment" or "in an embodiment" in various places throughout the specification are not necessarily all referring to the same aspect. Furthermore, the particular features, structures, or characteristics may be combined in any suitable manner in one or more aspects of the present disclosure.

Reference throughout the specification to integrated circuits is generally intended to include integrated circuit components built on semiconducting substrates, whether or not the components are coupled together into a circuit or able to be interconnected. Throughout the specification, the term "layer" is used in its broadest sense to include a thin film, a cap, or the like. The term "compound semiconductor" generally includes any semiconductor that has one or more materials outside column IV of the periodic table of the elements (e.g., carbon, silicon, germanium, etc.), or combinations of such materials. The term "high-frequency" in the context of operating wireless communication devices is meant in a relative sense, and is not limited to a designated frequency range (e.g., a particular "HF band" within the range of 3-30 MHz).

Reference throughout the specification to conventional thin film deposition techniques for depositing silicon nitride, silicon dioxide, metals, or similar materials include such processes as chemical vapor deposition (CVD), low-pressure chemical vapor deposition (LPCVD), metal organic chemical vapor deposition (MOCVD), plasma-enhanced chemical vapor deposition (PECVD), plasma vapor deposition (PVD), atomic layer deposition (ALD), molecular beam epitaxy (MBE), electroplating, electro-less plating, and the like. Specific embodiments are described herein with reference to examples of such processes. However, the present disclosure and the reference to certain deposition techniques should not be limited to those described. For example, in some circumstances, a description that references CVD may alternatively be done using PVD, or a description that specifies electroplating may alternatively be accomplished using electro-less plating. Furthermore, reference to conventional techniques of thin film formation may include growing a film in-situ. For example, in some embodiments, controlled growth of an oxide to a desired thickness can be achieved by exposing a silicon surface to oxygen gas or to moisture in a heated chamber.

Reference throughout the specification to conventional photolithography techniques, known in the art of semiconductor fabrication for patterning various thin films, includes a spin-expose-develop process sequence typically followed by an etch process. Alternatively or additionally, photoresist can also be used to pattern a hard mask, which, in turn, can be used to pattern an underlying film.

Reference throughout the specification to conventional etching techniques known in the art of semiconductor fabrication for selective removal of polysilicon, silicon nitride, silicon dioxide, metals, photoresist, polyimide, or similar materials includes such processes as wet chemical etching, reactive ion (plasma) etching (RIE), washing, wet cleaning, pre-cleaning, spray cleaning, chemical-mechanical planarization (CMP) and the like. Specific embodiments are described herein with reference to examples of such processes. However, the present disclosure and the reference to certain deposition techniques should not be limited to those described. In some instances, two such techniques may be interchangeable. For example, stripping photoresist may entail immersing a sample in a wet chemical bath or, alternatively, spraying wet chemicals directly onto the sample.

Specific embodiments are described herein with reference to examples of tunneling diodes and tunneling field effect transistor devices that have been produced; however, the present disclosure and the reference to certain materials, dimensions, and the details and ordering of processing steps are exemplary and should not be limited to those shown.

In the figures, identical reference numbers identify similar features or elements. The sizes and relative positions of the features in the figures are not necessarily drawn to scale.

Figure 2:
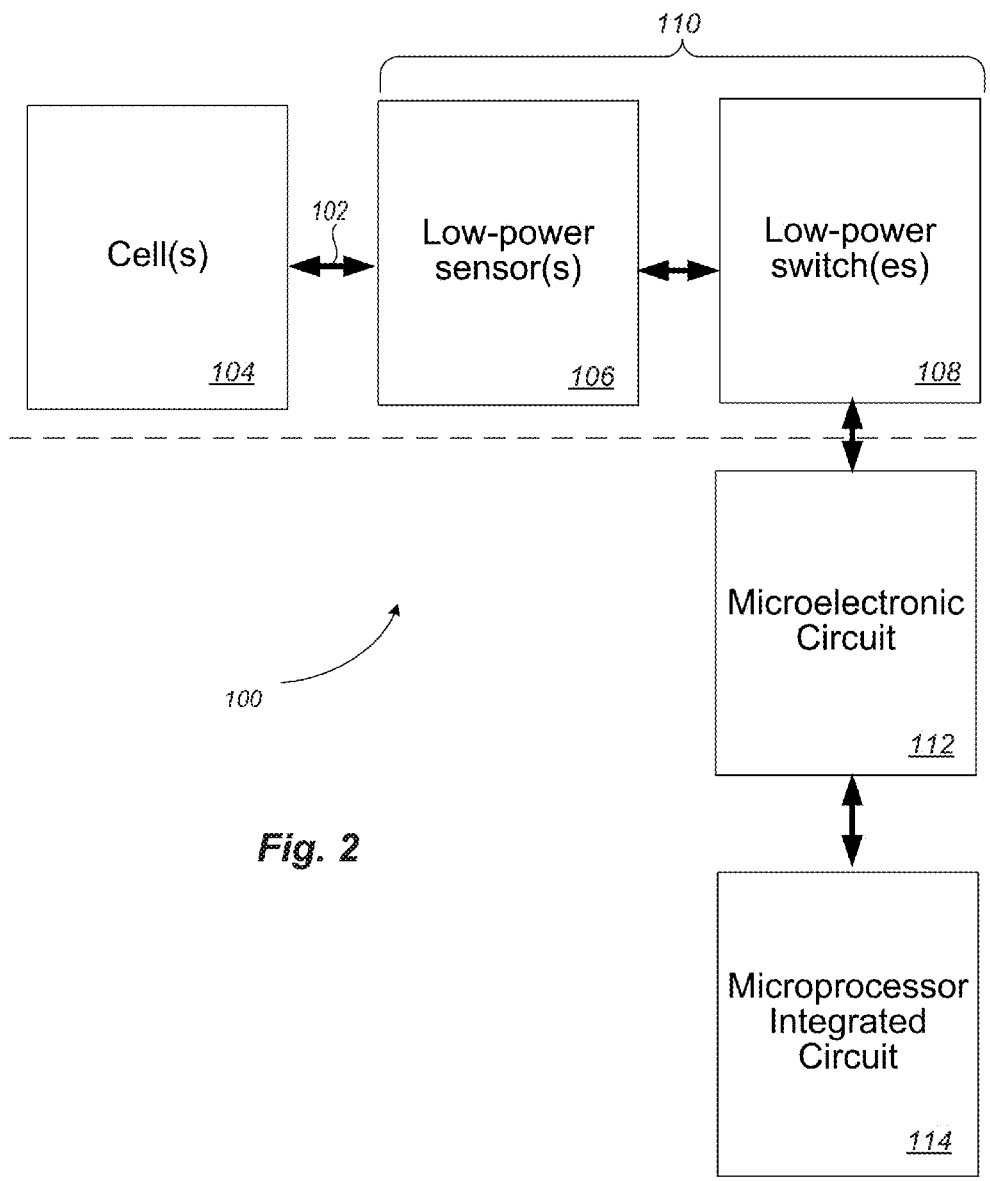
FIG. 2 is a block diagram illustrating one embodiment of a low power biological sensing system.

FIG. 2 shows a low power biological sensing system 100 according to one inventive embodiment. Such a low power system is feasible for use in detecting cellular activity (e.g., nerve impulses) associated with cells 104 of biological organisms, including live animals, human beings, and plants. The low power biological sensing system 100 can be built using one or more low power biocompatible sensor components 106 and one or more low power switching components 108. Such low power switching components 108 can be, for example, low power transistors or low power diodes. The low power switching components 108 can be part of, or can be coupled to a simple microelectronic signal processing circuit 112 wherein the low power components 106 and 108 are used at the cell interface 110. Such microelectronic signal processing circuits 112 can in turn be coupled to more complex arrangements of microelectronic components such as, for example, microprocessors or microprocessor integrated circuits 114. The focus of the system disclosed herein concerns the low power components 106 and 108 that interface directly with the biological cells 104.

Figure 3:
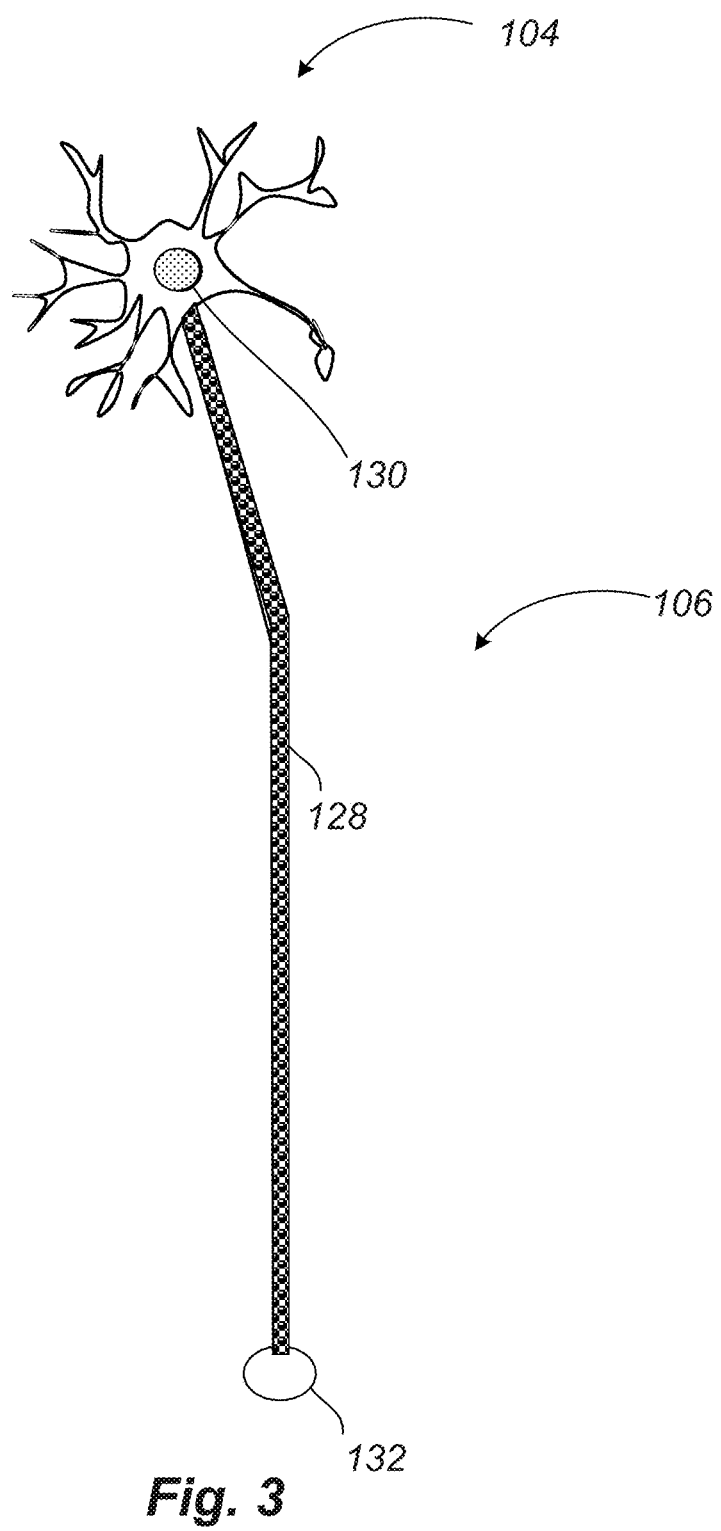
FIG. 3 is a pictorial diagram of a neuron coupled to a graphene nanosensor.

In one embodiment, the low power biocompatible sensor component 106 for use in the low power biological sensing system 100 as described herein is a neurological sensor that can establish an electrical interface with biological tissue, e.g., a nerve cell 104 (neuron), as illustrated in an exemplary embodiment shown in FIG. 3. The biocompatible neurological sensor includes a nanowire 128 (i.e., a nanometer-sized electrical conductor). The nanowire 128 is electrically responsive to an action potential of the nerve cell 104. Coupling of the nerve cell 104 to the nanowire 128 can entail, for example, use of an adhesive or a surface feature (e.g., surface roughness) that facilitates attachment to the nerve cell 104. Additionally or alternatively, the nanowire 128 can optionally include, for example, a conductive tip 130 that can be tapered to a point, or otherwise modified to facilitate insertion into the nerve cell 104. Such a conductive tip 130 can be removably coupled to the nanowire 128, thus permitting the nanowire 128 to be disconnected from a first conductive tip attached to a first nerve cell, and then connected to a second conductive tip attached to a second nerve cell. Additionally or alternatively, the nanowire 128 can flexibly attach to the nerve cell 104 by wrapping around at least a portion of the nerve cell 104. Alternatively, coupling of the nanowire 128 to the cell 104 can make use of any other methods known to those of skill in the art.

One preferred technique for coupling the nanowire 128 to the nerve cell 104 is the use of a specifically targeted phage. As is known, certain cells in the body have receptors which can more easily lock into or interact with compatible structures of certain chemistries, shapes, and molecular structures. A phage, using the broadest definition, is a small segment of biological tissue which can be custom designed to attach one end to a graphene nanowire and another end to a nerve cell. Therefore, according to one embodiment, a biological structure is attached to the tip 130 of the graphene nanowire 128, and the segments of biological tissue are custom designed for the graphene nanowire 128 to attach to the target cells. For example, the phage or other appropriate biological structure can be custom designed to link to a muscle cell, a white blood cell, fat tissue, or some other biological structure. The use of segments of biological structure to connect two elements to each other by having the appropriate receptors at each end are well known in the art, and therefore the details are not disclosed herein. See, for example, published U.S. Application 2008/0213663 to Hu et al. See also issued U.S. Pat. Nos. 7,960,721 and 7,902,639. Accordingly, using the teaching of these two U.S. patent documents, a biological segment can be constructed which attaches at one end to the graphene nanotube and at the other end to the desired biological living cell.

The biocompatible neurological sensor can further include a coupling device 132 attached to one end of the nanowire 128, the coupling device 132 being operable to electrically couple the nanowire 128 to the low power switching component 108. The coupling device 132 can be, for example, a connector, or a solder ball. Alternatively, the biocompatible neurological sensor can be directly coupled to the low power switching component 108 during fabrication of the switching component 108.

Existing nanowires 128 are made from many different materials, e.g., metals, semiconductors, or carbon. However, metal nanowires are not useful as biological cell sensors because they tend to damage the cells. Nanowires 128 made from graphene are desirable in a biological environment. Graphene nanowires that are already integrated into electronic circuits are generally commercially available and can be produced using conventional semiconductor processing technologies. However, such existing electronic circuits may not be appropriate for use in the low power biological sensing system 100.

Figure 4:
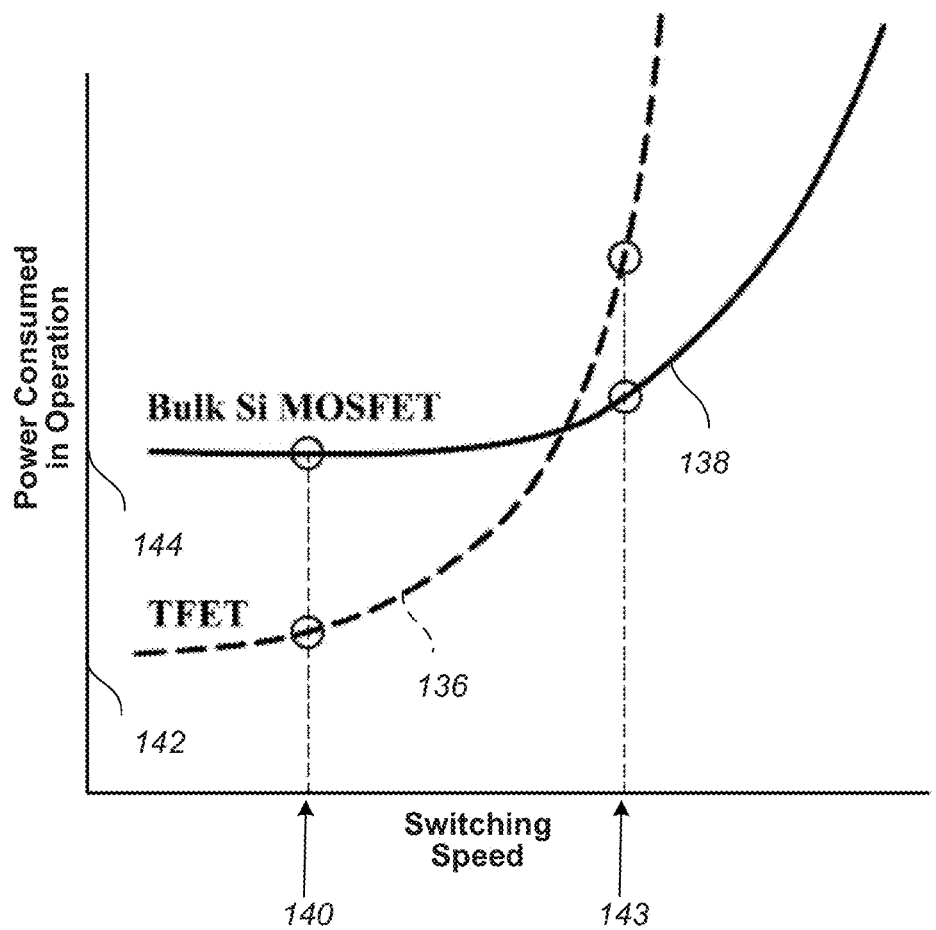
FIG. 4 is a plot of performance of a prior art TFET compared with that of a MOSFET at various energy levels.

In some embodiments of the low power biological sensing system 100, the low power switching component 108 is a tunneling field effect transistor (TFET). Generalized performance characteristics of a TFET are compared with those of a conventional metal-oxide-semiconductor FET (MOSFET) in FIG. 4. In particular, FIG. 4 shows a pair of graphs, 136 and 138, of energy vs. performance for both a TFET and a conventional bulk silicon transistor (MOSFET), respectively. When the TFET operates in a low power (low energy) mode, its performance 140 (e.g., switching speed) is equivalent to the MOSFET performance, but at a power level 142 that is about half that of the MOSFET device power level 144. Thus, at low power levels, the TFET is more efficient than the MOSFET, consuming significantly less power, and also dissipating less power as heat. At high switching speeds, however, it has been observed that the opposite is true. As the switching speed increases, the TFET consumes more power than the bulk silicon MOSFET, for example at speed point 143. Such advantageous performance characteristics that are specific to the low power regime make the TFET particularly well suited for use within biological organisms in which extremely fast switch speeds are not needed.

Figure 5C:
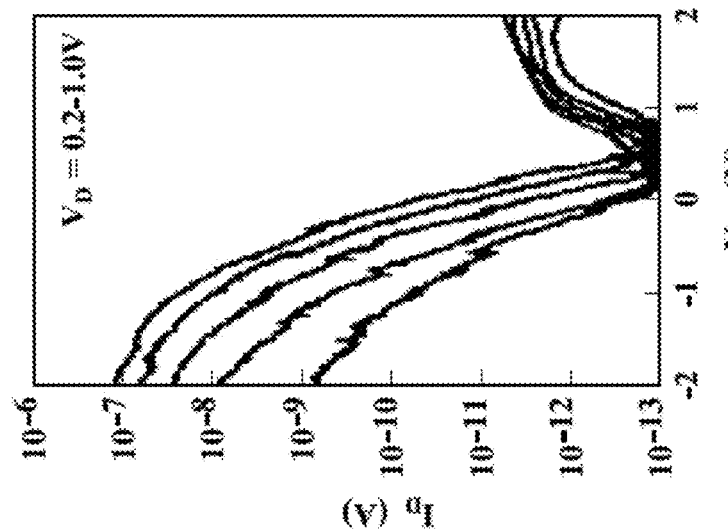
FIG. 5C is a family of I-V curves showing device turn-on for a reverse bias voltage applied to the gate.
Figure 5B:
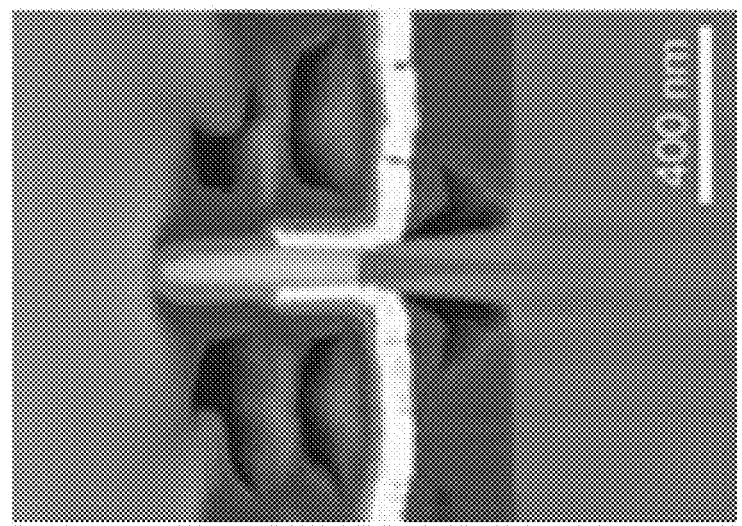
FIG. 5B is derived from a cross-sectional scanning electron micrograph of the TFET shown in FIG. 5A.
Figure 5A:
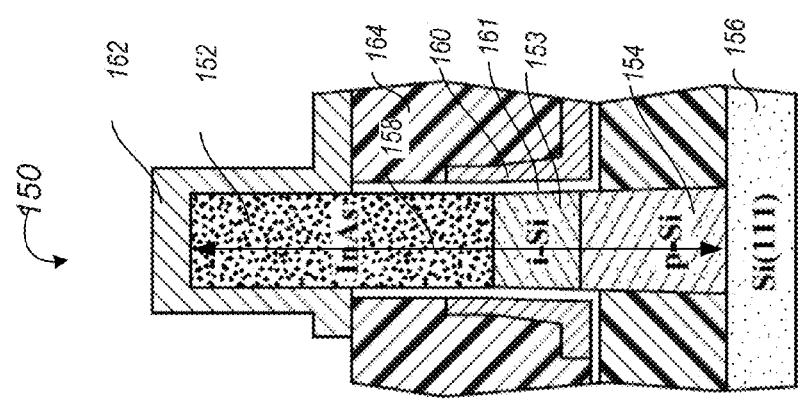
FIG. 5A is a cross-sectional schematic of a prior art TFET.

FIGS. 5A-5C show and describe an exemplary TFET 150 that can be used as the low power switching component 108, according to one embodiment. FIG. 5A shows a cross-sectional view of various layers of the TFET 150, as originally presented by Ionescu and Riel. The device illustrated in FIG. 5A is a p-i-n (p-type-intrinsic-n-type) device which includes an n-type indium arsenide ($n^+$-InAs) source 152, a region of intrinsic silicon (i-Si) 153, and a p-type silicon ($p^+$-Si) drain 154 stacked in a vertical configuration on a silicon substrate 156. Alternatively, the TFET 150 can be a p-n-p-n TFET, for example. Or, the TFET can be in a horizontal configuration. It is generally desirable for such a p-i-n device to have a high source doping level but a lower drain doping level. In one embodiment, the $n^+$ source doping concentration is about 1.0 E20 atoms/cm$^3$; the i-Si doping concentration is about 1.0 E17 atoms/cm$^3$; and the $p^+$ drain doping concentration is about 5.0 E18 atoms/cm$^3$ The channel of the TFET 150 (from the source 152 to the drain 154) is in the form of an epitaxially grown heterojunction nanowire 158. The heterojunction nanowire 158 desirably has a diameter within the range of about 2-200 nm and a height of about 8-800 nm. The source 152, intrinsic region 153, and drain 154 can be epitaxially grown sequentially from the silicon substrate 156 to thicknesses of 3-300 nm, 3-300 nm, and 8-800 nm, respectively. Growth of the heterojunction nanowire 158 can use a metalorganic chemical vapor deposition (MOCVD) process in which the InAs is doped by injection of disilane gas ($Si_2H_6$). In the example shown, the silicon substrate 156 has a (111) crystalline structure that facilitates epitaxial growth of the heterojunction nanowire 158. The silicon substrate 156 may include an oxide layer 163.

A wrap-around gate 160 surrounds the source-drain tunnel junction regions of the cylindrical heterojunction nanowire 158. The gate 160 can be a metal gate of thickness 2-200 nm, for example, made of tungsten (W). Alternatively, the gate 160 can include of titanium (Ti), titanium nitride (TiN), tantalum (Ta), tantalum nitride (TaN), copper (Cu), gold (Au), silver (Ag), or combinations thereof. The gate 160 is spaced apart from the channel by a gate dielectric 161 which can have a thickness in the range of, for example, 1-50 nm.

The gate dielectric 161 can be made of a high k dielectric material such as halfnium oxide ($HFO_2$) or an aluminum oxide ($Al_2O_3$) deposited using atomic layer deposition (ALD).

The TFET 150 also includes a metal contact 162 to the source 152, as well as a spacer layer 164 that provides isolation from neighboring devices. The spacer layer 164 can be made of silicon dioxide, silicon nitride, or an encapsulating layer such as benzocyclobutene (BCB). BCB can be deposited by spin-coating, and which can serve as an etch stop layer at various points during device fabrication. Additional details concerning fabrication of an exemplary TFET 150 are found in an IEEE publication by Riel et al. presented at the 2012 IEDM meeting, entitled, "InAs—Si Heterojunction Nanowire Tunnel Diodes and Tunnel FETs," which is hereby incorporated by reference in its entirety.

FIG. 5C is derived from an actual electron micrograph of the TFET, accompanied by a length scale. The exemplary heterojunction nanowire 158 is about 800 nm long and about 100 nm wide. Alternatively, a TFET made from a carbon nanotube, or from any one of various combinations of compound semiconductor materials, can be substituted for the InAs—Si nanowire. Such semiconductor materials can include, for example, InP, InGaN, InGaP, InAs, InAlAs, InGaAs, GaAs, GaN, AlN, AlGaAs, AlGaN, AlGaSb, AlSb, and the like.

FIG. 5D shows a family of current-voltage (I-V) curves for various source-drain biases (between 0.2 V and 1.0 V) of the TFET shown in FIGS. 5B and 5C. The TFET exhibits switching of the drain current from 0 A to about $10^{-7}$ A, or 0.1 pA, under a reverse bias voltage (i.e., negative values of applied gate voltage).

Figure 6A:
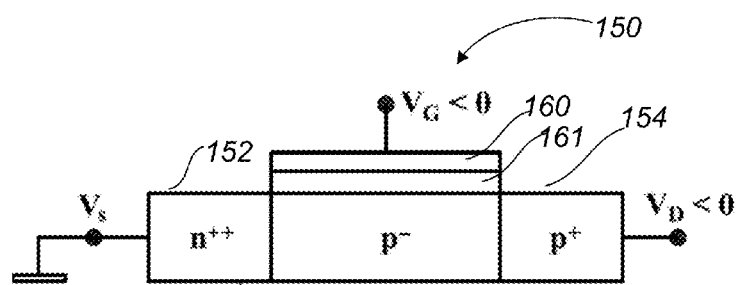
FIG. 6A is a cross-sectional schematic of the prior art TFET device of FIGS. 5A-5C.
Figure 6B:
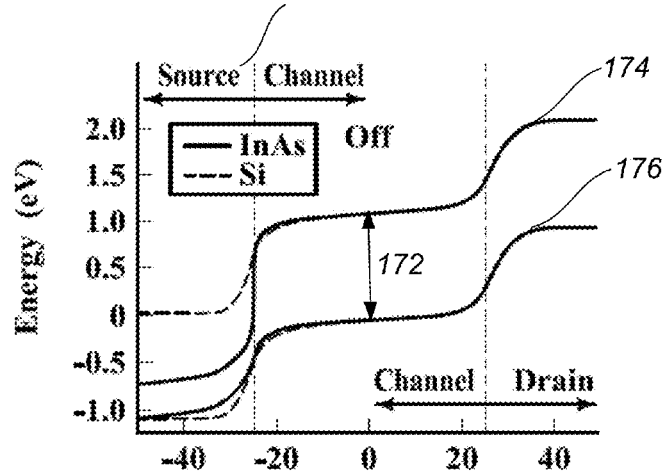
FIG. 6B is an energy band diagram corresponding to the off state for the TFET device shown in FIG. 6A.
Figure 6C:
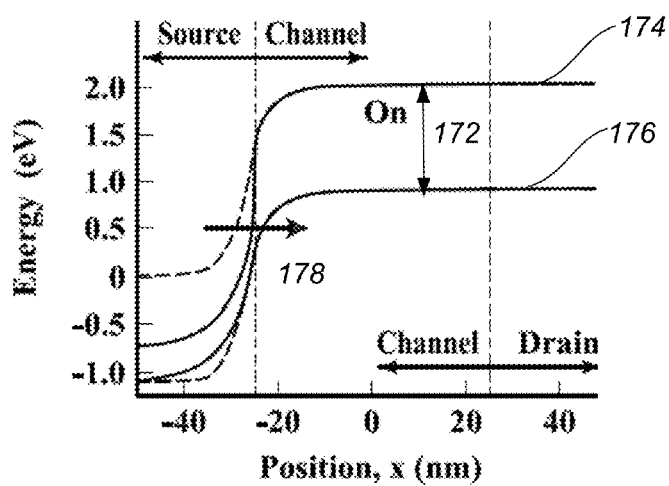
FIG. 6C is an energy band diagram corresponding to the on state for the TFET device shown in FIG. 6A.

The p-type TFET 150 described in FIGS. 4-5 is shown schematically in FIG. 6A. A TFET operates differently from a conventional MOSFET transistor in that charge carriers are injected into the TFET conducting channel via a process of quantum-mechanical tunneling. Tunneling can be understood by considering energetics at a heterojunction 170, i.e., a boundary between two different semiconductors, as shown in FIGS. 6B, 6C. Semiconductor materials (e.g., InAs and Si) each have a characteristic energy band gap 172 [the term "band gap" refers to the difference between the energy of conduction band electrons (free electrons) 174 and the energy of valence band electrons (atomically bound electrons) 176, i.e., the amount of energy needed to liberate valence electrons from atoms in the semiconductor crystal]. If the heterojunction 170 is such that one of the semiconductors (e.g., the Si drain 154) is made of a positively doped material having a narrow energy band gap while the other semiconductor (e.g., the InAs source 152) is made of a negatively doped material having a wide energy band gap, then when two such semiconductors are placed in contact with one another, their energy levels are discontinuous at the heterojunction 170, i.e., their conduction band energies do not coincide. Such a discontinuity in energy levels at the source-to-channel heterojunction 170 represents an energy barrier that prevents charge from entering the channel. However, tunneling can be made possible by applying a particular voltage $V_g$ to the gate 160 so as to distort the energy band structure of the channel region from that shown in FIG. 6B to that shown in FIG. 6C. Such a distortion lowers the energy barrier and allows current flow 178 from the source 152, across the heterojunction 170, into the channel, thereby switching the device on.

Figures 7A, 7B, 7C:
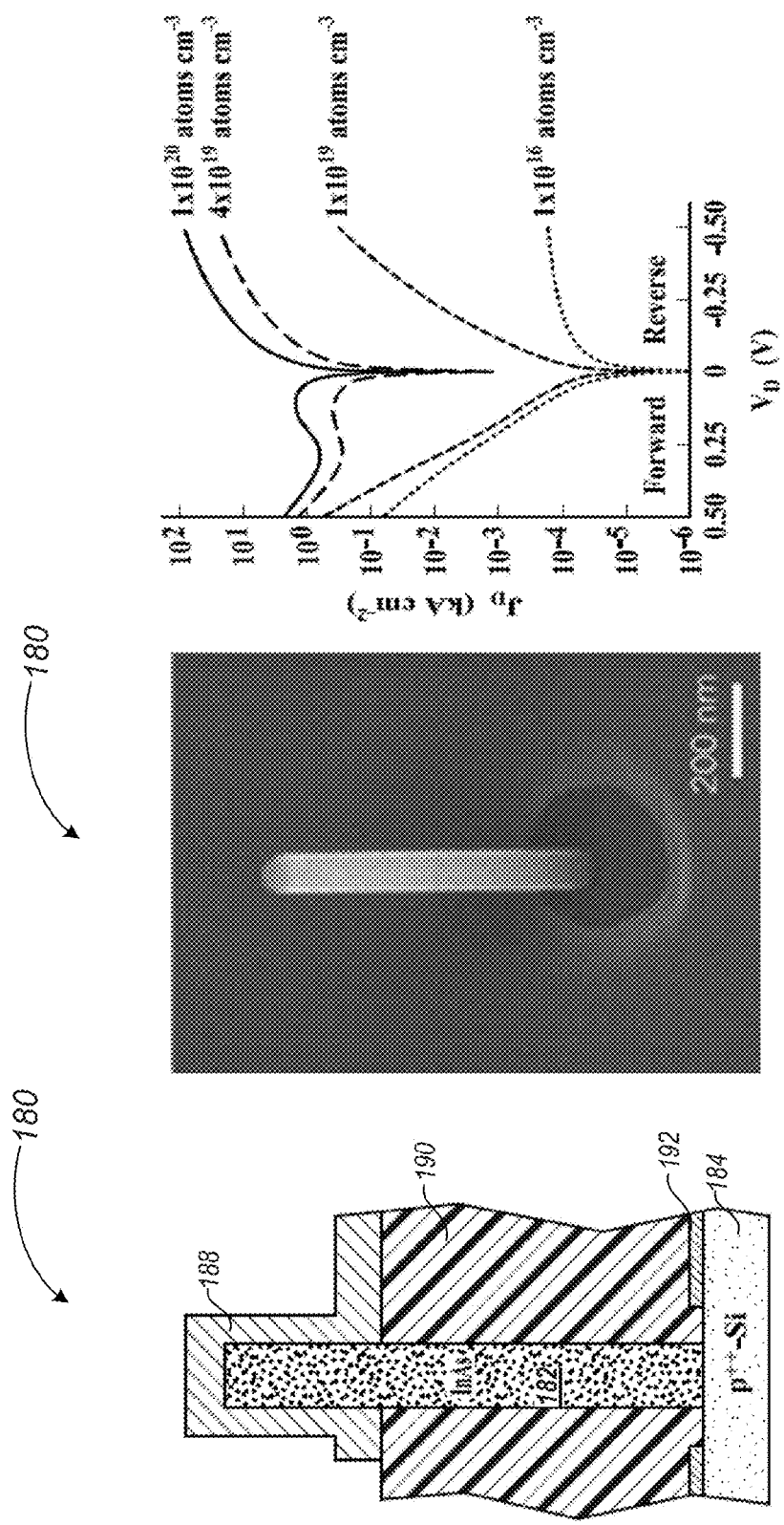
FIG. 7A is a cross-sectional schematic of a prior art tunneling diode.
FIG. 7B is derived from a cross-sectional scanning electron micrograph of the tunneling diode shown in FIG. 7A.
FIG. 7C is a family of J-V curves showing biasing characteristics for different substrate doping levels for the prior art tunneling diode shown in FIGS. 7A-7B.

FIGS. 7A-7C illustrate features of an exemplary tunneling diode 180 that can be used as the low power switching component 108, according to another embodiment. FIG. 7A shows a cross-sectional view of the tunneling diode 180, which includes an indium arsenide (InAs) n-type source 182, and a highly-doped silicon ($p^{++}$-Si) p-type substrate 184. The InAs—Si heterostructure is stacked in a vertical configuration on the silicon substrate 186. The tunneling diode 180 is in the form of an epitaxially grown nanowire, made by a process similar to the fabrication process described above for the TFET nanowire 158. In the example shown, the silicon substrate 186 has a (111) crystalline structure that facilitates epitaxial growth of the nanowire. The nanowire tunneling diode 180 also includes a metal contact 188 to the n-type source 182, a spacer layer 190, and an oxide layer 192. The spacer layer 190 provides isolation from neighboring devices. The spacer layer 190 can be made of silicon dioxide, silicon nitride, or an encapsulating layer such as BCB.

FIG. 7B is derived from an actual electron micrograph of the nanowire tunneling diode 180, accompanied by a length scale. The exemplary nanowire tunneling diode 180 is about 600 nm long and about 100 nm wide. Alternatively, a tunneling diode made from a carbon nanotube can be substituted for the InAs—Si nanowire tunneling diode 180. FIG. 7C shows a family of current density-voltage (J-V) curves for various silicon doping densities (in the range of about 1E16 atoms/$cm^3$-1E20 atoms/$cm^3$) of the nanowire tunneling diode 180 shown in FIGS. 7A and 7B. High current densities, up to 250 kA/$cm^2$, are achieved by maximizing the doping density of the $p^{++}$-Si.

Figure 8:
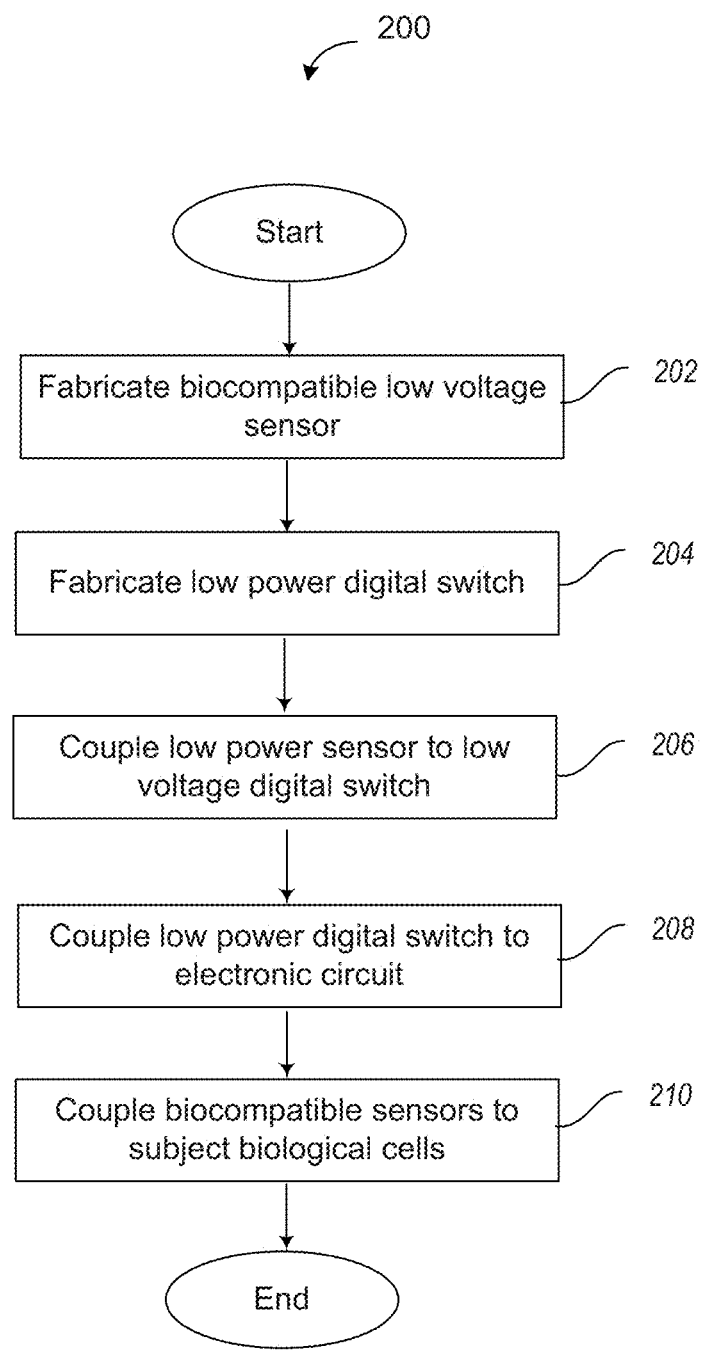
FIG. 8 is a flow chart showing steps in a method of constructing the low power biological sensor system shown in FIG. 2.

FIG. 8 shows steps in a method 200 of constructing the low power biological sensing system 100.

At 202, one or more low power biocompatible sensor components 106 are fabricated, preferably as graphene nanowires, nanotubes, nanoribbons, or other such nanostructures of comparable size to biological cells of interest. The biocompatible sensor components 106 transmit low voltage electrical signals in response to sensing action potentials associated with subject biological cells 104. In one embodiment the biological cells 104 having associated action potentials are neurons. However, in other embodiments, if it is discovered that other types of biological cells are electrically active, having associated action potentials, the low power biological sensing system 100 can be used to communicate with such cells other than neurons.

At 204, the low power switching component 108 is fabricated, separately from the low power biocompatible sensor components 106. The low power switching components preferably take the form of the nanowire tunneling diode 180 or the heterojunction nanowire 158, but are not so limited. Other switching devices that are capable of detecting low voltage signals transmitted by the biocompatible sensor components 106 can be substituted for those described herein.

At 206, one or more of the low power biocompatible sensor components 106 are coupled to one or more terminals of each low power switching component 108. Each diode provides two terminals (an anode and a cathode) to which the biocompatible sensor components 106 can be coupled, and the selection of where to couple it will be based on the desired electrical characteristics of the circuit. Each transistor provides up to three terminals (the gate, the source, and the drain) that can be coupled to the biocompatible sensor components 106. The terminals can be selected depending on whether the biocompatible sensor component 106 is to be used as an input or a load for a particular electrical circuit configuration. For example, the nanowire 128 can be coupled to a transistor gate, and therefore affect the turn-on characteristics of the transistor. In modern semiconductors, the threshold voltage for turning on a semiconductor continues to decrease, and a circuit can be custom designed with a threshold voltage in the 100 mV range or so. Nerve cells generally operate in the 70 mV range and have a threshold potential for firing in the 50-55 mV range. Accordingly, a transistor or a tunneling diode can be designed that is responsive to voltages in the range of 50-70 mV, so that input from an individual nerve cell will be sufficient to modify its operating characteristics and sense a signal in operation. Accordingly, the tunneling transistors are custom designed to have threshold voltages and operating characteristics in the range of 50-70 mV, and preferably to transition somewhere at approximately 65 mV, so they have similar transition characteristics to the threshold voltage of nerve cells firing in living biological tissue.

Generally, the voltage swing through an operation of a nerve cell is in the range of 100 mV or slightly more. It may, for example, transition from approximately −70 mV at rest to in the range of 30-40 mV or in some cases 50 mV at its peak transition. Accordingly, the transition voltage of an operating nerve cell is in the range of 100-110 mV.

Coupling the biocompatible sensor components 106 may entail inserting the coupling device 132 between the low power biocompatible sensor components 106 and the low power switching component 108. Alternatively, coupling the biocompatible sensor components 106 may entail soldering an end of the low power biocompatible sensor component 106 (e.g., graphene nanostructure) onto the contact pad of the low power switching component 108 (e.g., tunneling diode or TFET).

At 208, the low power switching component 108 is coupled to an electronic circuit. Signals produced by the low power switching component 108 can, for example, be saved as information in an electronic memory, or such signals can be used to drive other electronic components in the circuits 112 and 114, respectively. Additionally or alternatively, signals produced by the low power switching component 108 can be used to drive a radio transmitter to send sensed information about the cell 104 to a remote destination, via a wireless communication path.

At 210, each of the one or more low power biocompatible sensor components 106 is coupled to a different biological cell 104 to transmit signals to the low power switching component 108 in response to sensing an action potential associated with the biological cell 104. Coupling to the cell may entail use of a coupling device 130 such as an electrically conductive tip that adheres to the biological cell 104 using an adhesive, or by virtue of a surface feature (e.g., one or more micro-barbs, or surface roughness) of the conductive tip that facilitates attachment to the biological cell 104. Such a conductive tip can be removably coupled to the biocompatible neurological sensor to allow for coupling and de-coupling the graphene nanowire 128 in a modular fashion.

Figure 9:
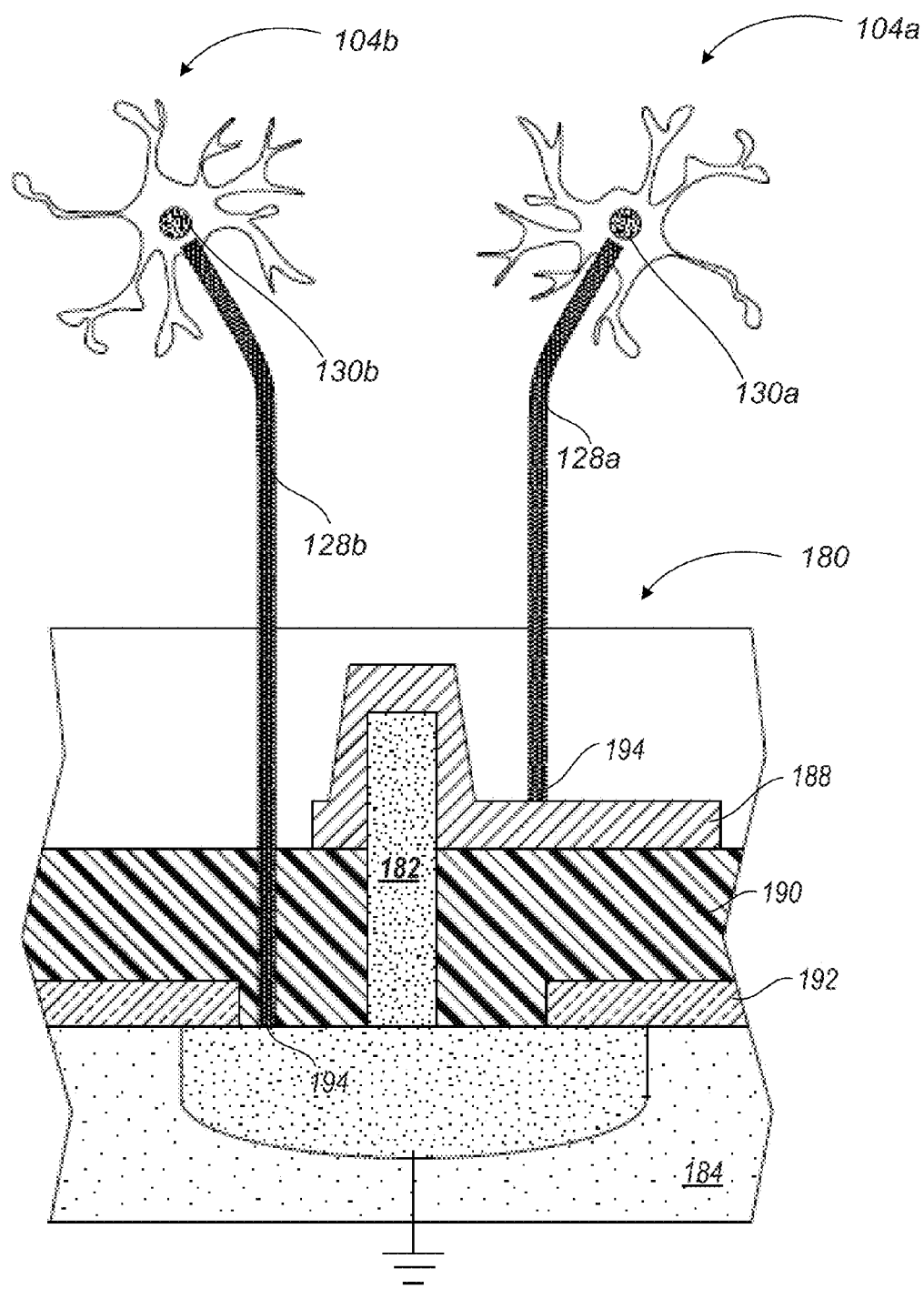
FIG. 9 shows a coupling scheme for two neurons connected to the tunneling diode shown in FIGS. 7A-7B.
Figure 10:
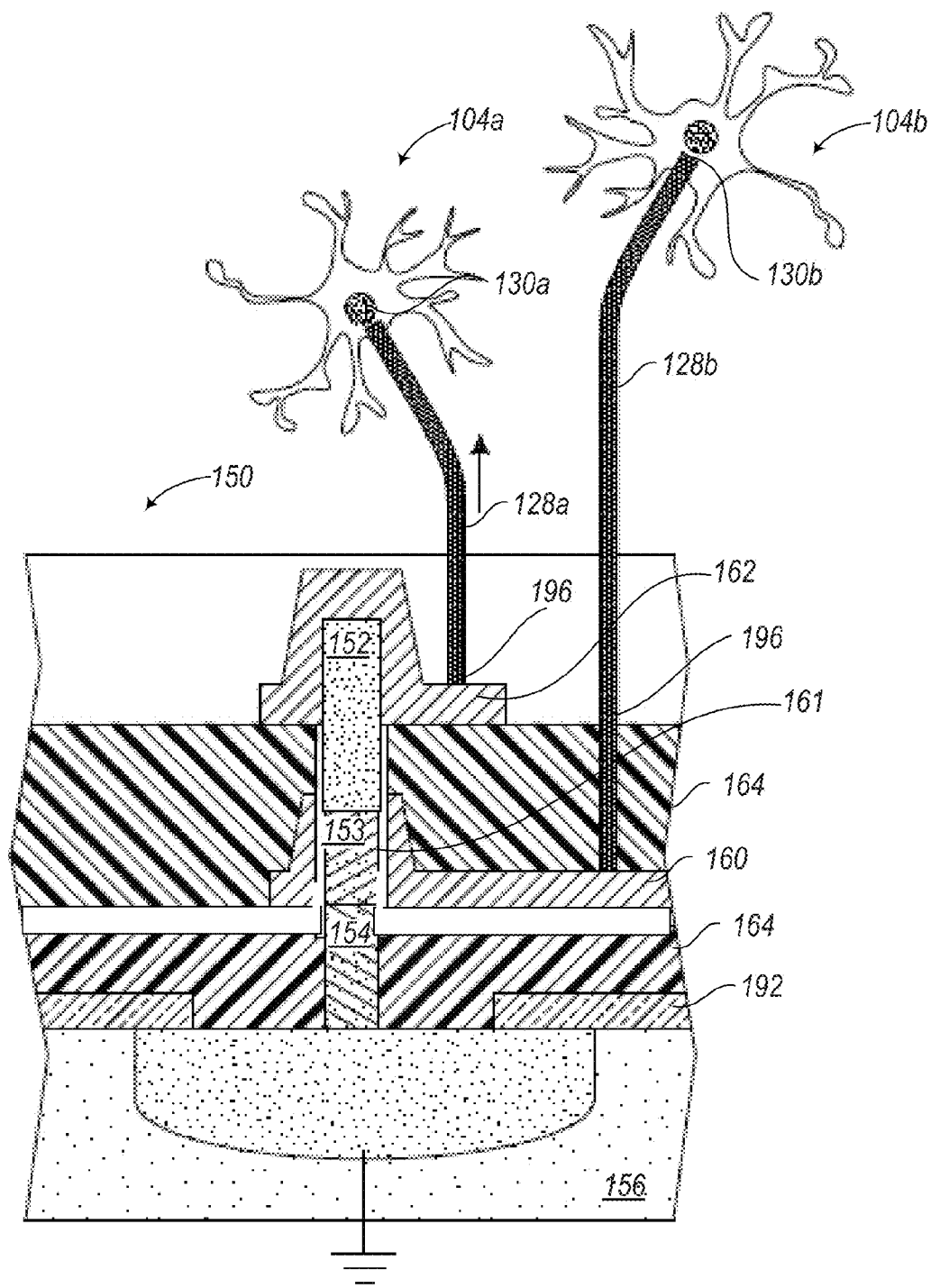
FIG. 10 shows a coupling scheme for two neurons connected to the TFET shown in FIGS. 5A-5B.
Figure 11:
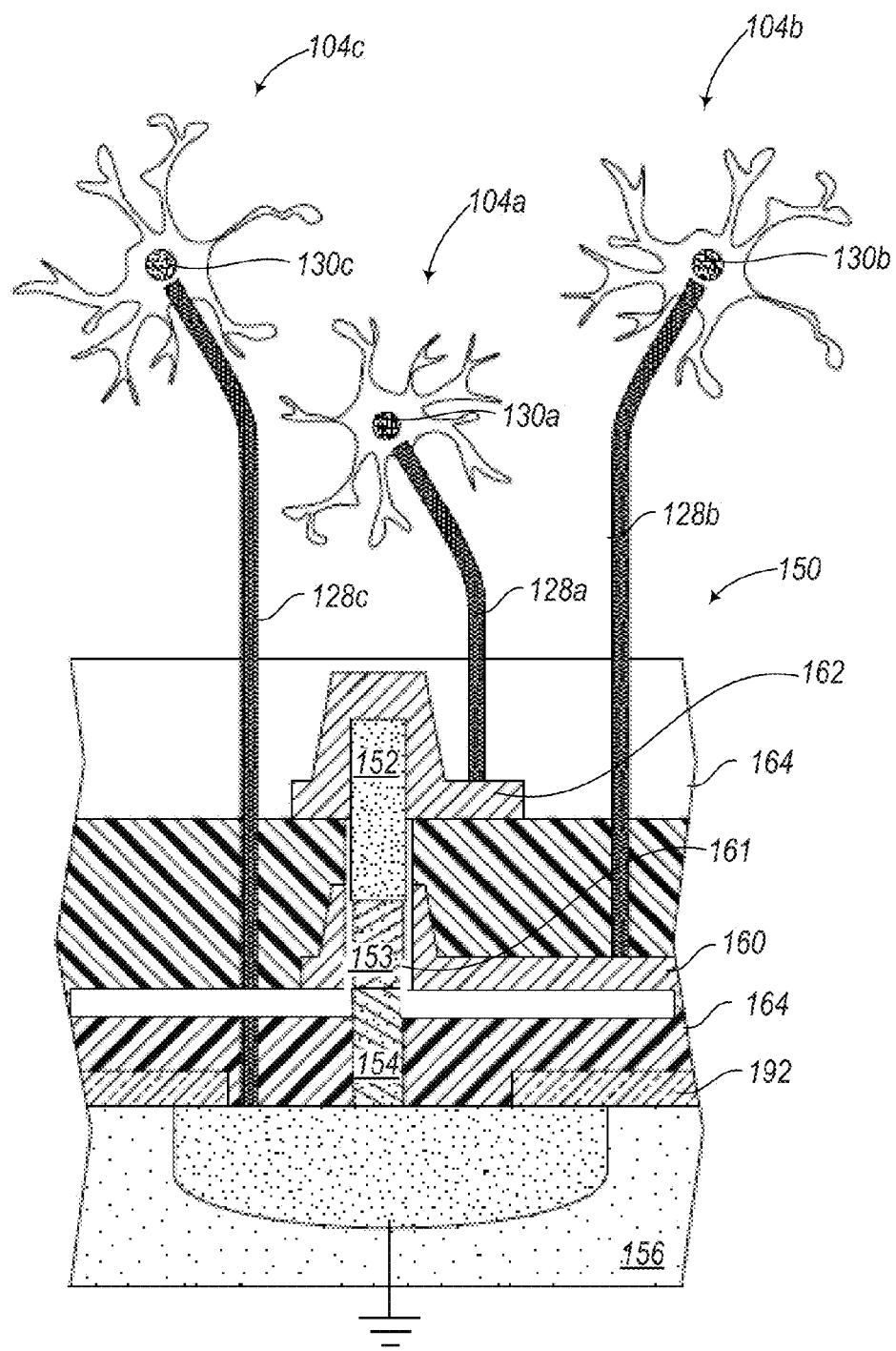
FIG. 11 shows a coupling scheme for three neurons connected to the TFET shown in FIGS. 5A-5B.

FIGS. 9-11 illustrate three exemplary embodiments of low power sensing systems 100 in which biocompatible sensor components 106 (e.g., graphene nanowires 128) are coupled to the low power switching components 108 (e.g., TFETs 150 or tunneling diodes 180) according to the method 200.

FIG. 9 shows an embodiment in which two nerve cells are coupled to the tunneling diode 180 via graphene nanowires 128. A first nerve cell 104a is coupled to a first graphene nanowire 128a, optionally using a first coupling device 130a. A second nerve cell 104b is coupled to a second graphene nanowire 128b optionally using a second coupling device 130b. The first graphene nanowire 128a is in turn coupled to the metal contact 188 to the source 182 of the tunneling diode 180. Likewise, the second graphene nanowire 128b extends through the spacer layer 190 and is coupled to the substrate 184 of the tunneling diode 180. If a sensed voltage of the first cell 104a exceeds a certain threshold value with respect to a sensed voltage of the second cell 104b, then the tunneling diode 180 switches on. Coupling the graphene nanowires 128a, 128b to the metal contact 188 and the substrate 184 entails forming openings in the intervening layers, for example, using a reactive ion etching process. After the contacts are opened, contact surfaces 194 may receive a silicidation treatment in which a metal silicide is formed such as $Ni_xSi_y$, $NixPt_ySi_z$, or $Ti_xSi_y$. Following the silicide treatment, the graphene nanowires 128 a,b may be inserted through the openings. Following insertion of the graphene nanowires 128, a thin layer of SiN or $SiO_xN_y$ film may be deposited at the contact point to fix the graphene nanowires 128 in place.

FIG. 10 shows an embodiment in which the TFET 150 is coupled to a pair of nerve cells 104a and 104b, via the graphene nanowires 128a, 128b, according to one embodiment. A first cell 104a is coupled to a first graphene nanowire 128a, optionally using a first coupling device 130a. Also shown is a second cell 104b coupled to a second graphene nanowire 128b, optionally using a second coupling device 130b. The first graphene nanowire 128a is in turn coupled to the metal contact 162 to the source 152 of the TFET 150. Likewise, the second graphene nanowire 128b extends through the spacer layer 164 and is coupled to the gate 160 of the TFET 150. Thus, if a sensed voltage of the second cell 104b exceeds a gate voltage threshold value, the TFET will turn on and current will flow from the source 152 to the drain 154. In this way, the state of the first cell 104a can be communicated to the second cell 104b. As previously mentioned, the TFET 150 is specifically built and designed to operate on voltage inputs in the range of 50-70 mV, which can be accomplished by careful and selective doping of impurities. The use of different levels of impurities to selectively control the threshold voltage of a TFET 150 or a transistor such as a MOSFET can be done using techniques for threshold adjustment, as is known in the art. Such threshold adjustments are more easily carried out for very small devices having geometries with minimum dimensions in the range of 30 nm or less. Such extremely small devices can more easily be tuned to operate at much lower voltages than the operating voltages of larger transistors and devices that have minimum dimensions (e.g., gate lengths) of 90 nm or more.

As a further alternative, the circuit configuration of the type shown in FIGS. 9 and 10 can be modified to be sensitive to a change in voltage in the range of 70 mV, even though the threshold voltage may be in the range of 400-500 mV. For example, rather than change the threshold voltage of the tunneling diode or the individual transistor, it is possible to preset the transistor to be approximately at its threshold voltage. Transistors are nonlinear devices, as are diodes. Therefore, if a voltage has been previously applied to the device to place it approximately at its threshold value, then the additional signal from the can modify the applied voltage by ±70 mV, thereby switching the transistor on or off by tipping it one way or the other. Generally, the polarity of nerve cells, when firing, can be either positive or a negative. Some nerve cells have a negative threshold of −40 mV--55 mV. A neuron has a resting potential of −70 mV. Accordingly, a change in the neuron from −70 mV to +40 mV is a fairly common reaction range, and it may vary from in the range of −60 mV to +50 mV, depending on the nerve cell and the particular biological condition.

The semiconductor device, whether tunneling diode or TFET, can have a preset voltage already applied to place it approximately at the switching location. As previously described, or alternatively asserted, the TFET can be constructed similarly to those used in sense amplifiers for memory cells. As is known, a sense amplifier for a memory cell such as a DRAM, SRAM, ROM, and the like is very sensitive to very small changes in voltage and current, i.e., significantly smaller changes than would be the threshold voltage. Commonly, such sense amplifier circuits are precharged to be balanced at a value very close to the threshold voltage for the transistors therein, on the verge of either turning off or turning on. When data is retrieved from the memory cell, whether a 1 or a 0, the associated voltage level is just enough to turn the sense amplifier either fully on or fully off, so that the reading takes place very quickly with only very small changes in voltage and/or current on the bit line. In a similar fashion, transistors coupled to the nanowire 128 can be connected in such a way that very small changes in the input can significantly modify the output, even individual transistor devices have threshold voltages in the 500 mV range. This is therefore a different alternative embodiment as opposed to the embodiment described above in which the transistor threshold voltage is modified. Here, a circuit is constructed from components that have a higher threshold voltage, but the circuit is operated in such a fashion as to be responsive to small input changes in the range of 100 mV and less.

Coupling the graphene nanowires 128a, 128b to the metal contact 162 and the gate electrode 160 entails forming openings in the intervening layers, for example, using a reactive ion etching process. After the contacts are opened, contact surfaces 196 may receive a silicidation treatment in which a metal silicide is formed such as $Ni_xSi_y$, $NixPt_ySi_z$, or $Ti_xSi_y$. Following the silicide treatment, the graphene nanowires 128 a,b may be inserted through the openings. Following insertion of the graphene nanowires 128, a thin layer of SiN or $SiO_xN_y$ film may be deposited at the contact point to fix the graphene nanowires 128 in place.

FIG. 11 shows an embodiment in which the TFET 150, is coupled to each of three nerve cells 104a, 104b, and 104c. A first cell 104a is coupled to a first graphene nanowire 128a, optionally using a first coupling device 130a. Also shown is a second cell 104b coupled to a second graphene nanowire 128b, optionally using a second coupling device 130b, and a third cell 104c coupled to a third graphene nanowire 128c, optionally using a third coupling device 130c. The first graphene nanowire 128a is in turn coupled to the metal contact 162 to the source 152 of the TFET 150. The second graphene nanowire 128b extends through the spacer layer 164 and is coupled to the gate 160 of the TFET 150. Finally, the third graphene nanowire 128c extends through the spacer layer 164 to the drain 154. Direct coupling of the graphene nanowires 128 to the TFET 150 (without use of a coupling device) can be accomplished during processing of the TFET 150 by opening contact holes in each of the metal contact 162, the gate 160, and the drain 154 during formation or polishing of such features as described above with reference to FIGS. 9 and 10.

If the sensed voltage at the second cell 104b exceeds a gate voltage threshold value, the TFET will turn on, causing current to flow from the source 152 to the drain 154. Thus, the second cell 104b (subject cell) controls the action potential of the other two cells 104a and 104c (object cells) via the TFET. In this way, a feedback control system can be set up in which the state of the second cell 104b can be used to control communication between the cells 104a and 104c, for example. Or, excess charge can be redistributed from one cell to another via the TFET to adjust the relative voltage levels of the cells. Such a redistribution of charge may have therapeutic effects that could substitute for drug treatment in certain circumstances (e.g., for electrically active organs such as the brain, heart, and neuromuscular system).

FIGS. 12A-12O show three exemplary alternative geometries of the graphene nanowire 128 in which the nanowire includes branches. For example, in FIG. 12A, the graphene nanowire embodiment 128c includes an orthogonal branch 170 that extends out from a main trunk 172 at substantially a right angle 173, forming a "T". In FIG. 12B, the graphene nanowire embodiment 128d includes a pair of angled branches 174 that extend out from a main trunk 172 in substantially opposite directions forming an "X". In FIG. 12A, the graphene nanowire embodiment 128e includes an angled branch 174 that extends out from the main trunk 172 at an acute angle 175, forming a "Y". Other similar geometries of a graphene nanowire that includes branches can be substituted for those shown in FIGS. 12A-12C. Such branched geometries may facilitate coupling the graphene nanowire 128 to the low power switching components 108 and/or coupling the graphene nanowire 128 to the biological cells 104 with or without use of a coupling device 130. Further discussion of such branched geometries is found in an article by M. Scarselli, P. Castrucci, and M. De Crescenzi, published in 2012, in *J. Phys: Condensed Matter* Vol. 24 No. 31, p. 313202.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

It will be appreciated that, although specific embodiments of the present disclosure are described herein for purposes of illustration, various modifications may be made without departing from the spirit and scope of the present disclosure. Accordingly, the present disclosure is not limited except as by the appended claims.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A low power sensing system suitable for use within a biological organism, the low power sensing system comprising:
one or more graphene sensors, each graphene sensor having a first end and a second end, each first end configured to couple to a nerve cell of the biological organism, the graphene sensors configured to sense electrical signals originating from within the nerve cell and, in response, output sensed electrical signals; and
an implantable tunneling field effect transistor (TFET) being electrically coupled to the second end of the one or more the graphene sensors, the TFET being configured to be activated by the sensed electrical signals, the TFET having a source terminal and a gate terminal, the source terminal being coupled to the second end of a first one of the graphene sensors, and the gate terminal being coupled to the second end of a second one of the graphene sensors.

2. The sensing system of claim 1 wherein the electrical signals are nerve cell impulses.

3. The sensing system of claim 1 wherein at least one of the graphene sensors is configured as a nanowire.

4. The sensing system of claim 1 wherein terminals of the TFET are arranged in a vertical orientation.

5. The sensing system of claim 1 wherein the first end of the first one of the graphene sensors is coupled to a first biological cell, and the first end of the second one of the graphene sensors is coupled to a second biological cell.

6. The sensing system of claim 1 wherein terminals of the TFET are coupled to different graphene sensors, each graphene sensor positioned in contact with a different nerve cell.

7. A biocompatible neurological sensor comprising:
   a first graphene nanowire that includes:
      a first end having an electrically conductive tip configured to be coupled to a first neuron; and
      a second end;
   a second graphene nanowire that includes:
      a first end having an electrically conductive tip configured to be coupled to a second neuron; and
      a second end; and
   an implantable tunneling field effect transistor (TFET) having a source terminal coupled to the second end of the first nanowire and having a gate terminal coupled to the second end of the second nanowire.

8. The biocompatible neurological sensor of claim 7 wherein the first and second graphene nanowires are formed from a rolled graphene sheet.

9. The biocompatible neurological sensor of claim 7, wherein the electrically conductive tip is removably coupled to the graphene nanowire.

10. The biocompatible neurological sensor of claim 7, wherein the first and second graphene nanowires are configured to flexibly attach to the first and second neurons respectively by wrapping around a portion of the neuron.

11. The biocompatible neurological sensor of claim 7 wherein the electrically conductive tip of the first and second graphene nanowires each includes an adhesive.

12. The biocompatible neurological sensor of claim 7 wherein the electrically conductive tip of the first and second graphene nanowires each includes a surface feature that facilitates attachment to the neuron.

13. A device comprising:
   a biocompatible sensor having a first graphene nanowire and a second graphene nanowire, the graphene nanowires each having a first end and a second end, the first end of the first graphene nanowire configured to be coupled to a first nerve cell and the first end of the second graphene nanowire configured to be coupled to a second nerve cell, the biocompatible sensor configured to transmit low voltage electrical signals in response to an action potential from the first and second nerve cell;
   an implantable tunneling field effect transistor (TFET) configured to respond to the low voltage electrical signals, a first terminal of the TFET being coupled to the second end of the first graphene nanowire and a second terminal of the TFET being coupled to the second end of the second graphene nanowire; and
   an electronic circuit coupled to the TFET.

14. The device of claim 13 wherein the electronic circuit includes an electronic memory configured to store information about the first and second nerve cells.

15. The device of claim 13 wherein the TFET is configured to be coupled to a third nerve cell, the TFET being configured to control an action potential of the third nerve cell based on the low voltage electrical signals from the biocompatible sensor.

16. The sensing system of claim 1 wherein the TFET includes a drain terminal coupled to the second end of a third one of the graphene sensors.

17. The biocompatible neurological sensor of claim 7, further comprising:
   a third graphene nanowire that includes:
      a first end having an electrically conductive tip configured to be coupled to a third neuron; and
      a second end, the second end coupled to a third terminal of the TFET.

18. The device of claim 13, further comprising:
   a third graphene nanowire having a first end and a second end, the first end of the third graphene nanowire configured to be coupled to a first nerve cell, a third terminal of the TFET being coupled to the second end of the third graphene nanowire.

19. The device of claim 13 wherein the action potential of the first and second nerve cells are nerve cell impulses.

20. The device of claim 13 wherein terminals of the TFET are arranged in a vertical orientation.

* * * * *